(12) United States Patent
Hayes

(10) Patent No.: US 8,494,351 B1
(45) Date of Patent: Jul. 23, 2013

(54) DECORATIVE LIGHTING WITH SCENT DISPENSERS

(76) Inventor: Cheryl A. Hayes, Las Vegas, NV (US)

( * ) Notice: Subject to any disclaimer, the term of this patent is extended or adjusted under 35 U.S.C. 154(b) by 153 days.

(21) Appl. No.: 13/099,626

(22) Filed: May 3, 2011

Related U.S. Application Data

(60) Provisional application No. 61/331,068, filed on May 4, 2010.

(51) Int. Cl.
*A61M 16/00* (2006.01)
*A24F 25/00* (2006.01)

(52) U.S. Cl.
USPC ........... 392/393; 392/386; 392/390; 392/391; 392/394; 392/395; 392/396; 392/397; 392/398; 362/122; 362/96; 362/161; 362/810

(58) Field of Classification Search
USPC ......... 392/386, 390, 391, 393–398, 403–406; 362/96, 161, 810
See application file for complete search history.

(56) References Cited

U.S. PATENT DOCUMENTS

| | | | | |
|---|---|---|---|---|
| 1,403,548 A | * | 1/1922 | Gudeman | 422/125 |
| 1,981,650 A | * | 11/1934 | Larsen | 362/92 |
| 2,005,229 A | * | 6/1935 | Loos et al. | 128/203.27 |
| 2,124,543 A | * | 7/1938 | Clyne | 392/393 |
| 2,152,466 A | * | 3/1939 | Clyne | 392/395 |
| 3,080,624 A | * | 3/1963 | Weber, III | 422/125 |
| 3,959,642 A | * | 5/1976 | Turro | 362/92 |
| 4,171,754 A | * | 10/1979 | Rosado | 222/646 |
| 4,579,717 A | * | 4/1986 | Gyulay | 422/125 |
| 4,647,428 A | * | 3/1987 | Gyulay | 422/4 |
| 5,902,101 A | * | 5/1999 | Palmer et al. | 431/202 |
| 5,908,231 A | | 6/1999 | Huff | |
| 6,044,202 A | | 3/2000 | Junkel | |
| 6,155,695 A | * | 12/2000 | Sealy | 362/237 |
| 7,246,919 B2 | * | 7/2007 | Porchia et al. | 362/276 |
| 7,318,659 B2 | * | 1/2008 | Demarest et al. | 362/253 |
| 7,503,675 B2 | * | 3/2009 | Demarest et al. | 362/253 |
| 7,604,378 B2 | * | 10/2009 | Wolf et al. | 362/253 |
| 7,913,688 B2 | * | 3/2011 | Cross et al. | 128/203.26 |
| 8,137,630 B2 | * | 3/2012 | Jorgensen | 422/123 |
| 8,281,514 B2 | * | 10/2012 | Fleming | 43/129 |
| 2006/0147353 A1 | | 7/2006 | Wang | |
| 2006/0188238 A1 | * | 8/2006 | Kent | 392/394 |
| 2010/0177506 A1 | | 7/2010 | Van Dyn Hoven | |

* cited by examiner

*Primary Examiner* — Joseph M Pelham
*Assistant Examiner* — Jimmy Chou
(74) *Attorney, Agent, or Firm* — Kenehan & Lambertsen, Ltd.; John C. Lambertsen

(57) ABSTRACT

A fragrance generator provides a scent dispenser for mounting on a light emitter of a decorative light, such as those used at holidays. A silicone rubber scented sleeve is placed over and around a cylindrical light emitter. Upon energizing the decorative light, the heat generated by the light emitter warms the scented sleeve and thereby enhances the rate of scent emission from the scented sleeve. An optional scent reservoir formed at one end of the scented sleeve enables the retention of additional amounts of liquid fragrance oil(s). Placement of the light emitter within and extending it throughout the sleeve, and into the fragrance reservoir, results in a further enhancement in amount and duration of scent emission.

4 Claims, 1 Drawing Sheet

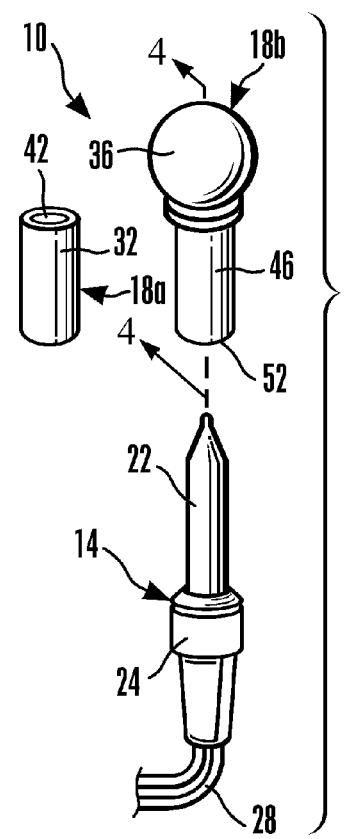
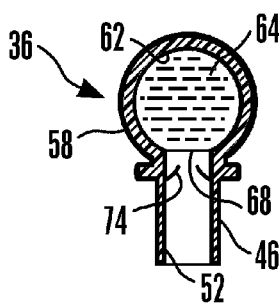
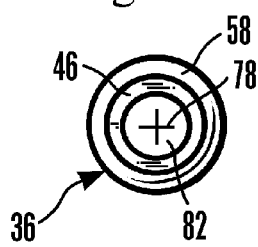
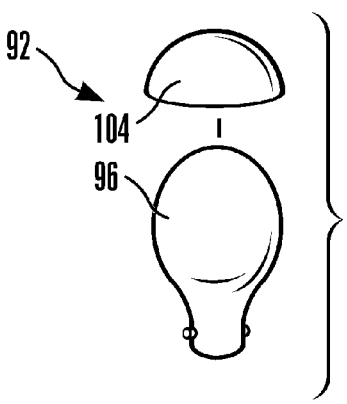
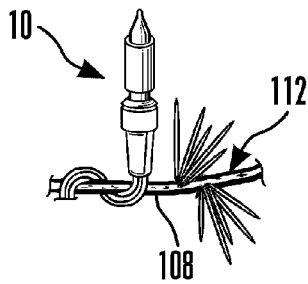

DECORATIVE LIGHTING WITH SCENT DISPENSERS

RELATED APPLICATIONS

The present application claims priority under 35 U.S.C. §119(e) to U.S. Provisional Patent Application Ser. No. 61/331,068, filed May 4, 2010, which is incorporated by reference herein for all that it contains.

BACKGROUND OF THE INVENTION

1. Field of the Invention

The present invention relates to scenting and fragrancing devices and, more particularly, to a heated fragrancing device. More specifically, the present invention relates to a decorative light casing that releases a fragrance when warmed.

2. Description of the Prior Art

The importance of utilizing pleasing scents to create positive personal moods and feelings is well known, and air freshener products are now widely marketed by many different vendors. Holidays are particularly associated by most people with scents and smells from their past—pines for Christmas trees and spices from holiday foods. Bychowski in U.S. Pat. No. 3,945,568 provides the scent of pine using Christmas tree ornaments containing pine-scented liquids. In all such scent generators, it is important for a user to be able to regulate the dispersion of scent. It is particularly advantageous to be able to enhance the amount of scent generated during specific, desired times—such as when company is visiting, and to be able to reduce the amount of scent at other times—such as when the house is asleep. The ability to reduce scent generation is particularly useful—if for no other reason than to extend the life of the scent-generator.

SUMMARY OF THE INVENTION

Through utilization of decorative lighting, combined with use of fragrant sleeves, caps, and reservoirs, dissemination of the desired scent is enhanced by the heat generated by the light bulbs. When used as directed, the product material enables scent generation without the burning, melting or leaking of the fragrant oils. Preferably fabricated using high-temperature silicone rubber, such material enables use throughout a temperature range of from −94 degrees (F.) to +392 degrees (F.). Additionally, such preferred material is able to handle higher temperatures than natural or man-made rubber, and it will maintain its flexibility and resiliency over time.

The present invention can utilize any fragrance or combination of fragrances, ranging from subtle to very strong. Such fragrance oils can be added to the silicone material before the curing process—or after curing by soaking the product in the fragrant oil (the product will fill and swell).

As presently contemplated the silicone product can be made in virtually any color or combination of colors, as well as including embeds for decorative purposes. The material can be molded into various sizes to accommodate different brands of lights, and can include a silicone reservoir of the fragrant oil(s) to provide additional fragrance life and strength. Such fragrance reservoir can be made in various shapes and sizes, with a valve added to reduce the chances of leakage. Imprints and raised designs can be included for decorative purposes—with appropriate decorations provided for any holiday, season or occasion.

The present invention enables a simple change-out when a change in fragrance(s) is desired, and can be used indoors or outside. Use of bug repellant, alone or included in the fragrant oil is contemplated where desired by the user.

Essential oils can be used with the fragrance or alone to provide for their various effects. For example, lavender can be utilized to induce sleep, citrus for energy, and so forth.

The utilization of more of these fragrant silicone rubber sleeves, caps, and reservoirs provides for a stronger scent—with smaller areas requiring less of these products. While fragrance can permeate smaller areas, large areas require more products—or the present fragrance sleeves, caps, and reservoirs can be limited in number to limit the extent of fragrance to smaller areas. In very large areas, the present sleeves, caps, and reservoirs will provide fragrance in the immediate vicinity only.

Utilizing strings of decorative lights that are typically used during the holidays, in one embodiment of the present invention a scent reservoir is tied to a decorative light. An outside casing for a decorative light is provided, the casing fabricated of a material that readily absorbs desired fragrance. Additionally, the casing remains in fluid communication with a reservoir that holds the desired fragrance.

A miniature light is placed inside this casing, with the tip of the bulb extending beyond an outer end of the casing, permitting the bulb to extend into a fragrance reservoir. When lit, the bulb generates heat that warms the scent reservoir causing a greater amount of scent to be emitted and encourages a flow of the fragrance from the reservoir into the casing. The casing is also warmed by the lit bulb, with the casing material releasing a greater amount of fragrance when warmed. Thus when turned on by a user the decorative lighting distributes an increased amount of a pleasing scent in comparison to when the lighting is not operating.

The decorative light casing invention is safe, inexpensive, and easily adaptable to the miniature light strings currently on the market. The casings and fragrance reservoirs can be scented with a desired fragrance(s) to correspond with any holiday season.

An alternative embodiment of the present invention relates in general to an alternative decorative light that uses the heat from a light bulb to dispense fragrance oil. In a safe, simple, and inexpensive manner, this embodiment of the present invention provides one-piece unit that distributes a pleasing scent when the bulb is turned on.

This alternative embodiment of the present invention is fabricated in a cap-shaped design of a material that readily absorbs fragrance oil and does not melt from the heat of the light bulb. Upon placement on the light bulb the configuration of this fragrance dispenser creates a suction force that permits a user to selectively maintain attachment of the dispenser to the light bulb, keeping the dispenser securely in place. When desired a user can easily remove the dispenser by releasing the suction. This dispenser is particularly useful when placed upon decorative holiday lighting or upon night lights. This dispenser may be used on any light source employing light bulbs of no more than 5 watts of power.

A still further alternative design for generating pleasing scents utilizes a light cover made of a porous material that readily absorbs desired scent. Fabricated in a sleeve configuration, this light cover may be directly received by and fastened to a miniature light bulb. The light bulb provides a heat source when turned on, which increases the rate of scent emission during those times when the light is illuminated.

The invention of a sleeve fragrance dispenser is safe, easy and inexpensive. It is adaptable to miniature light strings currently on the market. The invention can be scented with fragrance to correspond with any holiday/season.

All of the various presently preferred embodiments of the present invention are readily adapted for use on decorative lighting of the type used with Christmas trees. The scent sleeve and scent cap fragrance dispensers can easily be used with existing decorative lighting, and replaced as required when fragrance chemicals become depleted—or a difference fragrance is desired. A fragrance sleeve and reservoir combination enables scent emission over extended duration.

It is to be understood that the invention is not limited in its application to the details of construction and the arrangement of components described hereinafter and illustrated in the drawing figures. Those skilled in the art will recognize that various modifications can be made without departing from the scope of the invention.

BRIEF DESCRIPTION OF THE DRAWINGS

Embodiments in accordance with the present invention are described below in connection with the accompanying drawing figures.

FIG. 1 is an exploded perspective view of alternative light casings as received by and upon a decorative light in accordance with the present invention.

FIG. 2 is a perspective view of a sleeve light casing received by and upon a decorative light.

FIG. 3 is a perspective view of a sleeve and fragrance reservoir light casing received by and upon a decorative light.

FIG. 4 is a cross-sectional view taken along line 4-4 of FIG. 1 of a sleeve and fragrance reservoir light casing in accordance with the present invention.

FIG. 5 is a bottom plan view of a sleeve and fragrance reservoir light casing in accordance with the present invention.

FIG. 6 is an exploded perspective view of a fragrance cap as received by and upon a light bulb in accordance with the present invention.

FIG. 7 is a partial perspective view of a decorative light having a sleeve light casing, the decorative light shown attached to and supported by a pine tree branch.

DETAILED DESCRIPTION OF THE PREFERRED EMBODIMENTS

Reference is now made to the drawings wherein like structures refer to like parts throughout. In FIG. 1 a fragrance generator 10 consists of a decorative light 14 and a scent dispenser 18a, 18b. The decorative light 14 includes a cylindrical light emitter 22, an emitter base 24, and electrical wires 28, the latter providing the electricity necessary to power the light emitter 22. The light emitter can be incandescent, LED—or and of such other lighting technology as is considered suitable for use as a decorative light.

The scent dispensers 18a, 18b are shown as two alternative, preferred embodiments: a scented sleeve 32; and a scent reservoir 36. The scented sleeve is generally cylindrically shaped having an inner sleeve through-bore 42. The scent reservoir 36 includes a projecting reservoir sleeve 46 that is similarly provided with a reservoir sleeve through-bore 52.

When assembled the scented sleeve 32 is received by and upon the cylindrical light emitter 22, as is shown in FIG. 2, or, alternatively, the scent reservoir 36 is received by and upon the light emitter 22, as is shown in FIG. 3. Turning first to FIG. 2, the scented sleeve 32 is placed over the cylindrical light emitter 22, which is received within the sleeve through-bore 42. Energizing the light emitter causes heat to be generated, which in turn warms the scented sleeve resulting in an increased amount of fragrance emission.

As is shown in FIG. 3, the scent reservoir 36 is placed over the light emitter 22, with the light emitter 22 preferably extending through the reservoir sleeve through-bore 52 and into the scent reservoir 36. Upon energizing the light emitter 22 light and heat energy are produced, the latter resulting in the heating of the scent reservoir 36 and the reservoir sleeve 46. This heat energy in turn results in the increased generation of fragrance emission.

As is best shown in FIG. 4 the scent reservoir 36 consists of an outer globe 58 that defines an interior spherical reservoir 62 that is suitable for containing an amount of liquid fragrance oil 64. The spherical reservoir 62 is provided an entry opening 68 formed therein.

A presently preferred embodiment includes an entry valve 74 located within the reservoir sleeve 46 at a location substantially adjacent the entry opening 68 of the spherical reservoir 62. Although various types of valve structures are possible and are considered as lying within the present invention, as is shown in FIG. 5 an X-shaped flap valve 78 formed in a valve membrane 82 is presently preferred. Such valving—X-shaped or otherwise, assists in preventing leakage of the fragrance oil 64 within the spherical reservoir during shipment and storage of the scent reservoir 36.

When in use (reference is to FIGS. 1, 3, 4 and 5), the light emitter 22 is inserted within the reservoir sleeve through-bore 52, to a position where the light emitter 22 extends entirely through the reservoir sleeve 46, through the globe reservoir entry valve 74 and the spherical reservoir entry opening 68, with an end segment 86 of the light emitter 22 (see FIG. 3) projecting into the interior of the spherical reservoir 58.

A scent cap fragrance generator 92 is shown in FIG. 6 and provides a further alternative, presently preferred embodiment. A larger wattage bulb 96, such as within the 5-7 watt range, is provided a fragrance cap 104 that is received by and rests upon the larger wattage bulb 96. The fragrance cap 104 is preferably configured in a manner such that its placement upon the larger wattage bulb 96 results in the creation of a slight suction force that retains the fragrance cap 104 in position thereon.

FIG. 7 illustrates a possible use of the fragrance generator 10, showing it attached to the bough 108 of a holiday decoration 112—such as a Christmas tree or wreath. It is to be understood and appreciated that although the scented sleeve is shown on the decorative light, the present invention contemplates the use of scent reservoirs and fragrance caps as well—each of the present inventive alternatives providing enhanced scent emissions.

In a presently preferred embodiment the scent generators may be fabricated of high temperature silicone rubber having dimensions for use on such decorative lights as "Clear Mini Lights" distributed and sold by Home Depot of Atlanta, Ga., 5-watt bulbs include such as Model No. C75WC sold by Kmart Corporation of Troy, Mich., and 7-watt bulbs such as Model No. JMP9(7)-25 E158949 sold by Wal-Mart Stores, Inc., of Bentonville, Ark. Scented sleeves and reservoir sleeves are sold to match the bulb, and are thus provided in various dimensions. Such variations in size include (by way of example and not limitation) 0.5-1 mm in length with an outer diameter of 4-8 mm and an inner diameter of 3-4 mm. Scent reservoirs are provided in dimensions wherein the globe reservoir measures 1.5-2 mm, a sleeve length of 1 mm, outer diameter of 4-8 mm and inner diameters of 3-4 mm. Suitable fragrance oils include those sold by Natures Garden of Wellington, Ohio (www.naturesgardencandles.com) and the "Scent Moods" fragrances marketed by V.I. Reed & Cane of Rogers, Ark. (www.reeddiffusers.org).

My invention has been disclosed in terms of a preferred embodiment thereof, which provides decorative lighting with scent dispensers that is of great novelty and utility. Various changes, modifications, and alterations in the teachings of the present invention may be contemplated by those skilled in the art without departing from the intended spirit and scope thereof. It is intended that the present invention encompass such changes and modifications.

The invention claimed is:

1. A scent dispenser, comprising:
   a sleeve having a cylindrical configuration and a through-bore formed along a central axis thereof, said through-bore of suitable dimension to slidably receive a cylindrical light emitter of a decorative light,
   a liquid fragrance oil releasably absorbed by said sleeve in a manner such that an emission rate of said liquid fragrance oil from said sleeve is enhanced upon application of heat energy to said sleeve,
   an interior reservoir formed in a first end of said sleeve, wherein said interior reservoir is in fluid communication with said through-bore formed in said sleeve, and
   an interior reservoir entry valve formed within said through-bore, whereby energizing said cylindrical light emitter applies heat energy to said sleeve when slidably received thereon.

2. A scent dispenser as described in claim 1, wherein said sleeve is fabricated out of a high temperature silicone rubber.

3. A fragrance generator, comprising:
   a sleeve having a cylindrical configuration and a through-bore formed along a central axis thereof, said through-bore of suitable dimension to slidably receive a cylindrical light emitter of a decorative light, wherein said sleeve is fabricated out a high temperature silicone rubber;
   a liquid fragrance oil releasably absorbed by said sleeve in a manner such that an emission rate of said liquid fragrance oil from said sleeve is enhanced upon application of heat energy to said sleeve;
   an interior reservoir formed in a first end of said sleeve, wherein said interior reservoir is in fluid communication with said through-bore formed in said sleeve; and
   an interior reservoir entry valve formed within said through-bore, whereby energizing said cylindrical light emitter applies heat energy to said sleeve when slidably received thereon.

4. A fragrance generator as described in claim 3, wherein said interior reservoir entry valve is located substantially adjacent said interior reservoir.

\* \* \* \* \*